(12) United States Patent
Ferguson

(10) Patent No.: US 7,728,286 B2
(45) Date of Patent: Jun. 1, 2010

(54) SYSTEM AND METHOD FOR MEASURING PROPERTIES OF EXTRACTED EARTH FORMATION MATERIAL USING PULSE NEUTRON SPECTROSCOPY

(75) Inventor: Grant Victor Ferguson, Calgary (CA)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 12/207,129

(22) Filed: Sep. 9, 2008

(65) Prior Publication Data

US 2010/0059667 A1   Mar. 11, 2010

(51) Int. Cl.
*G01V 5/10* (2006.01)
(52) U.S. Cl. .................... 250/269.6; 250/255
(58) Field of Classification Search ......... 250/255, 250/269.6
See application file for complete search history.

(56) References Cited

U.S. PATENT DOCUMENTS

2007/0241275 A1* 10/2007 Guo et al. ............ 250/269.1
2007/0246649 A1* 10/2007 Jacobi et al. .......... 250/269.6
2008/0156975 A1*  7/2008 Kieschnick ............. 250/255

OTHER PUBLICATIONS

Richard Pemper, et al. "A New Pulsed Neutron Sonde for Derivation of Formation Lithology and Mineralogy". SPE 102770. 2006 SPE Annual Technical Conference and Exhibition held in San Antonio, Texas, U.S.A., Sep. 24-27, 2006.
Grant Ferguson, "Application of Pulsed Neutron Elemental Spectroscopy Measurements in Heavy Oil and Shale Gas Reservoir Evaluation". Back to Exploration. 2008 CSPG CSEG CWLS Convention. pp. 521-524.

* cited by examiner

*Primary Examiner*—David P Porta
*Assistant Examiner*—Mark R Gaworecki
(74) *Attorney, Agent, or Firm*—Cantor Colburn LLP

(57) ABSTRACT

A method for monitoring a composition of hydrocarbon material extracted from an earth formation is disclosed. The method includes: extracting the hydrocarbon material from the earth formation; diverting a portion of the hydrocarbon material into a container, the container including a pulse neutron spectroscopy tool disposed therein; emitting a plurality of pulses of high-energy neutrons from the pulse neutron spectroscopy tool into the portion of the hydrocarbon material and inducing at least one gamma ray spectrum from the portion; detecting the at least one gamma ray spectrum at the pulse neutron spectroscopy tool; and calculating a composition of the hydrocarbon material based on the at least one gamma ray spectrum. A system for monitoring a composition of hydrocarbon material extracted from an earth formation is also disclosed.

20 Claims, 3 Drawing Sheets

SYSTEM AND METHOD FOR MEASURING PROPERTIES OF EXTRACTED EARTH FORMATION MATERIAL USING PULSE NEUTRON SPECTROSCOPY

BACKGROUND

Hydrocarbons such as oil and gas found in various earth formations vary in form and require different methods of extraction. Oil and gas found in reservoirs or otherwise occurring having a low enough viscosity are extracted by drilling wells into the earth formation. More viscous occurrences of hydrocarbons, such as oil sands formations, require alternate techniques, such as steam assisted gravity drainage ("SAGD") and surface mining.

Surface mining techniques involve extracting surface material above the tar sands formation, i.e., overburden, as well as the underlying tar sands. Various methods of extraction, such as shovel and truck operations, are employed to extract the bitumen feed stock and transport it to a processing location where crude oil is extracted from the bitumen.

The variability of the bitumen feed stock in surface mining operations poses considerable cost and production issues. Changes in composition affect the rate at which bitumen can be extracted and/or processed, and thus affect the rate and cost of oil production therefrom. In addition, drastic changes in composition can potentially cause breakdowns or failures, resulting in significant production losses and costs.

BRIEF DESCRIPTION OF THE INVENTION

A method of monitoring a composition of hydrocarbon material extracted from an earth formation, the method comprising: extracting the hydrocarbon material from the earth formation; diverting a portion of the hydrocarbon material into a container, the container including a pulse neutron spectroscopy tool disposed therein; emitting a plurality of pulses of high-energy neutrons from the pulse neutron spectroscopy tool into the portion of the hydrocarbon material and inducing at least one gamma ray spectrum from the portion; detecting the at least one gamma ray spectrum at the pulse neutron spectroscopy tool; and calculating a composition of the hydrocarbon material based on the at least one gamma ray spectrum.

A system for monitoring a composition of hydrocarbon material extracted from an earth formation includes: a container configured to receive a portion of the hydrocarbon material extracted from the earth formation; a protective housing disposed in the container; a pulsed neutron spectroscopy tool disposed in the housing and including at least one neutron generator configured to emit a stream of high energy neutrons into an interior of the container, and at least one radiation detector configured to detect at least one gamma ray spectrum produced in response to the stream of high energy neutrons; and a processor configured to calculate a composition of the hydrocarbon material based on the at least one gamma ray spectrum.

BRIEF DESCRIPTION OF THE DRAWINGS

The following descriptions should not be considered limiting in any way. With reference to the accompanying drawings, like elements are numbered alike.

DETAILED DESCRIPTION OF THE INVENTION

Figure 1:
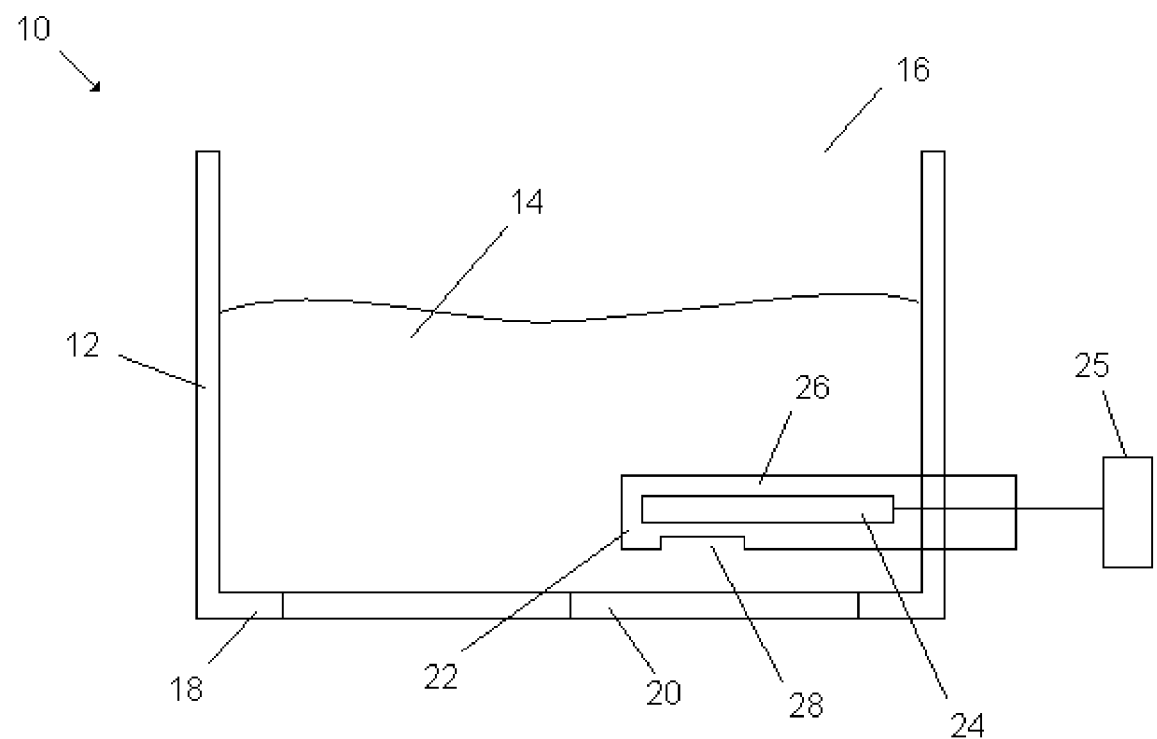
FIG. 1 is a cross-sectional view of an embodiment of a formation composition monitoring system.

Referring to FIG. 1, an exemplary embodiment of a system for monitoring hydrocarbon material extracted from an earth formation utilizing pulse neutron spectroscopy is indicated generally at 10. As described herein, "hydrocarbon material" includes any type of hydrocarbon or material containing hydrocarbons. An example of a hydrocarbon material includes crude oil existing in a formation. Crude oil can exist in the formation with various viscosities or exist in combination with various materials. As used herein, "bitumen" refers to any combination of petroleum and matter in the formation and/or any mixture or form of petroleum, specifically petroleum naturally occurring in a formation that is sufficiently viscous as to preclude well techniques commonly used for free flowing oil. An example of bitumen is a tar sands or oil sands formation. Bitumen and surrounding formation materials are collectively referred to as "ore". Although some embodiments described herein are described in conjunction with extracting bitumen, the embodiments are not limited. The embodiments described herein may be used for hydrocarbons of any viscosity and any combination of hydrocarbon and formation material.

The system 10 includes a container 12 for retaining a portion of ore and/or bitumen 14 collected during extraction of the ore and/or bitumen 14 from an earth formation. As described herein, "formations" refer to the various features and materials that may be encountered in a subsurface environment. In one embodiment, the container 12 is a container having dimensions similar to a standard dumpster container. The container 12 includes an open end 16 by which the ore 14 can be disposed in the container and a closed end 18. In one example, the closed end 18 is located at a bottom portion of the container 12 and includes a slidable or hinged door 20, such as a trapdoor. The configuration of the open end 16, the closed end 18 and the door 20 are exemplary and are not limited. Any suitable configuration for allowing the ore 14 to be disposed in the container 12 and subsequently removed may be used.

The system 10 also includes a measurement assembly 22 including a pulsed neutron spectroscopy tool 24 disposed therein. The tool 24 is disposed within a housing 26 made of a suitable material, such as steel, to withstand the weight of the ore 14. The housing 26 includes an opening 28 that allows for a section of the ore 14 to be bombarded with neutrons and for the tool 24 to detect gamma rays produced from the neutron bombardment. In one embodiment, the opening 28 is located at a bottom location of the housing 26 and configured so that gravity prevents the ore 14 from entering the opening 28 when the ore 14 is loaded into the container 12.

In one embodiment, the housing 22 extends from an interior of the container 12 to an exterior of the container 12. In this embodiment, the housing 22 includes an opening or access door configured to allow access to the tool 24 from the exterior of the container 12, so that the container is readily removable without the need to empty the container 12 or directly access the interior of the container 12. In one embodiment, the tool 24 is in operable communication with a remote processor 25.

Figure 2:
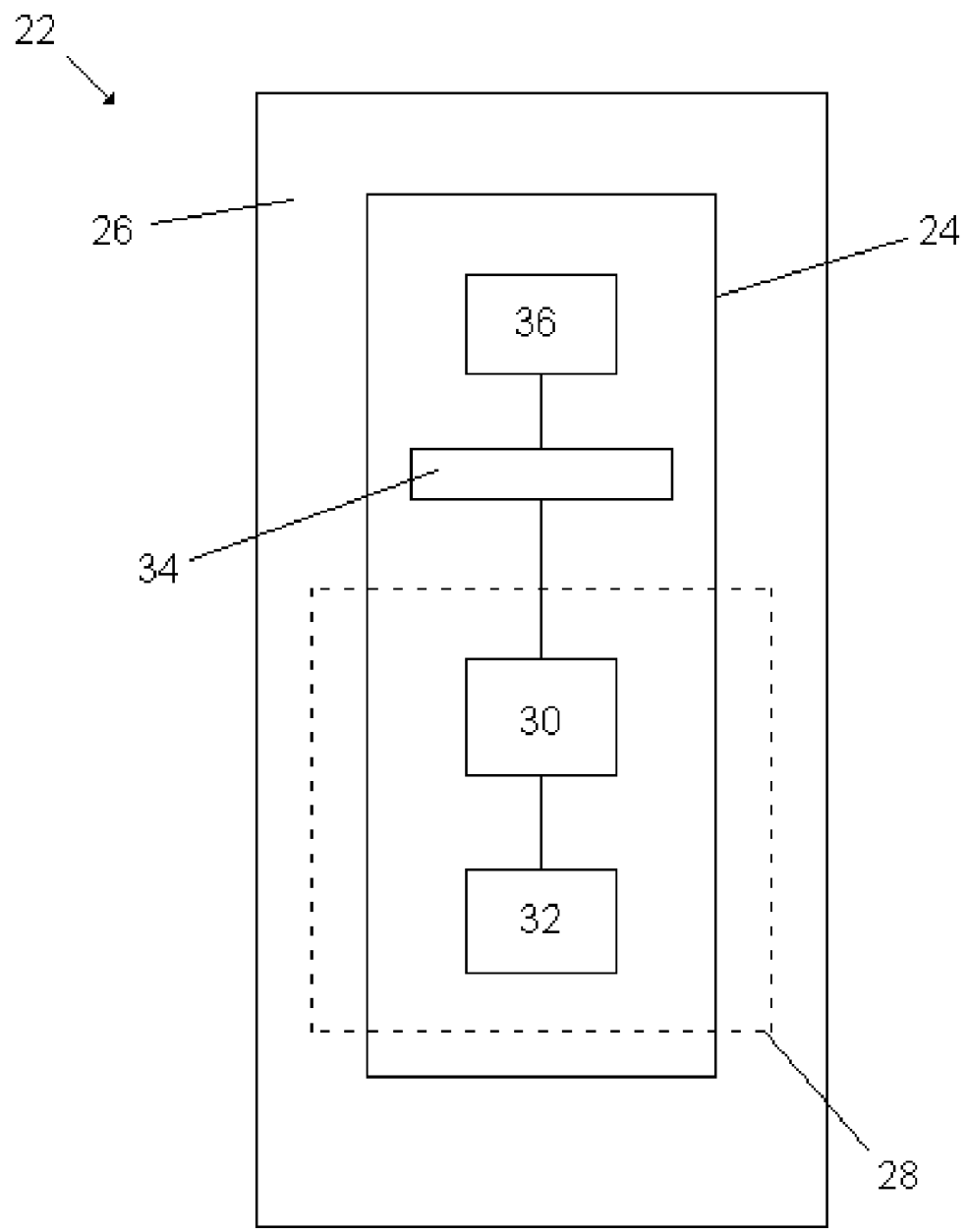
FIG. 2 is a cross-sectional view of a portion of a measurement assembly of the formation composition monitoring system of FIG. 1.

Referring to FIG. 2, the tool 24 includes at least one neutron source 30 for emitting a pulsed stream of neutrons toward an exterior of the tool 24 and toward, for example, the ore 14 or an earth formation. An example of the neutron source 30 is a high-energy neutron generator, having an energy of, for example, 14.1 MeV. In use, the neutrons bombard nuclei in the ore 14, inducing characteristic gamma rays through inelastic neutron scattering, fast-neutron reactions and neutron capture.

At least one radiation detector 32 detects an inelastic spectrum and/or a capture spectrum. The inelastic spectrum is the gamma ray spectrum emitted due to inelastic neutron scattering and fast-neutron reactions that generally occur very soon after each neutron pulse, and the capture spectrum is detected based on capture events that occur later.

In one embodiment, the inelastic spectrum is provided for calculation of a concentration or weight percentage of elemental carbon (C) in the formation as well as concentrations or weight percentages of elements or other constituents including Silica ($SiO_2$), Sulfur (S), Chlorine (Cl), Magnesium (Mg) and Aluminum (Al). The elemental weight fractions of such constituents can be used to measure the lithology of the ore 14 and measure concentrations of selected elements in the ore.

In one embodiment, the tool 24 is a Formation Lithology Explorer (FLEx)$^{sm}$ tool or other suitable tool for performing pulsed neutron spectroscopy. Although the tool 24 is described herein as disposed within the container 12, the tool 24 may be configured to be disposed at any suitable location, such as at a surface or near surface location of a formation, a location within an underground mine within the formation, and a location within a borehole disposed in the formation.

In one embodiment, the tool 24 includes an electronics unit 34 such as a processor to record, process and/or transmit the resultant gamma ray and/or composition data. In one embodiment, a power source 36 is included, such as a battery assembly, to power the electronics unit 34, the generator 30 and/or the detector 32. Alternatively, a remote power source and/or the remote processor 25 is operatively coupled to the tool 24.

In one embodiment, the remote processor 25 and/or the tool 24 include components as necessary to provide for storing and/or processing data collected from various sensors therein. Exemplary components include, without limitation, at least one processor, storage, memory, input devices, output devices and the like. The remote processor 25 optionally is configured to control the tool 24.

Figure 3:
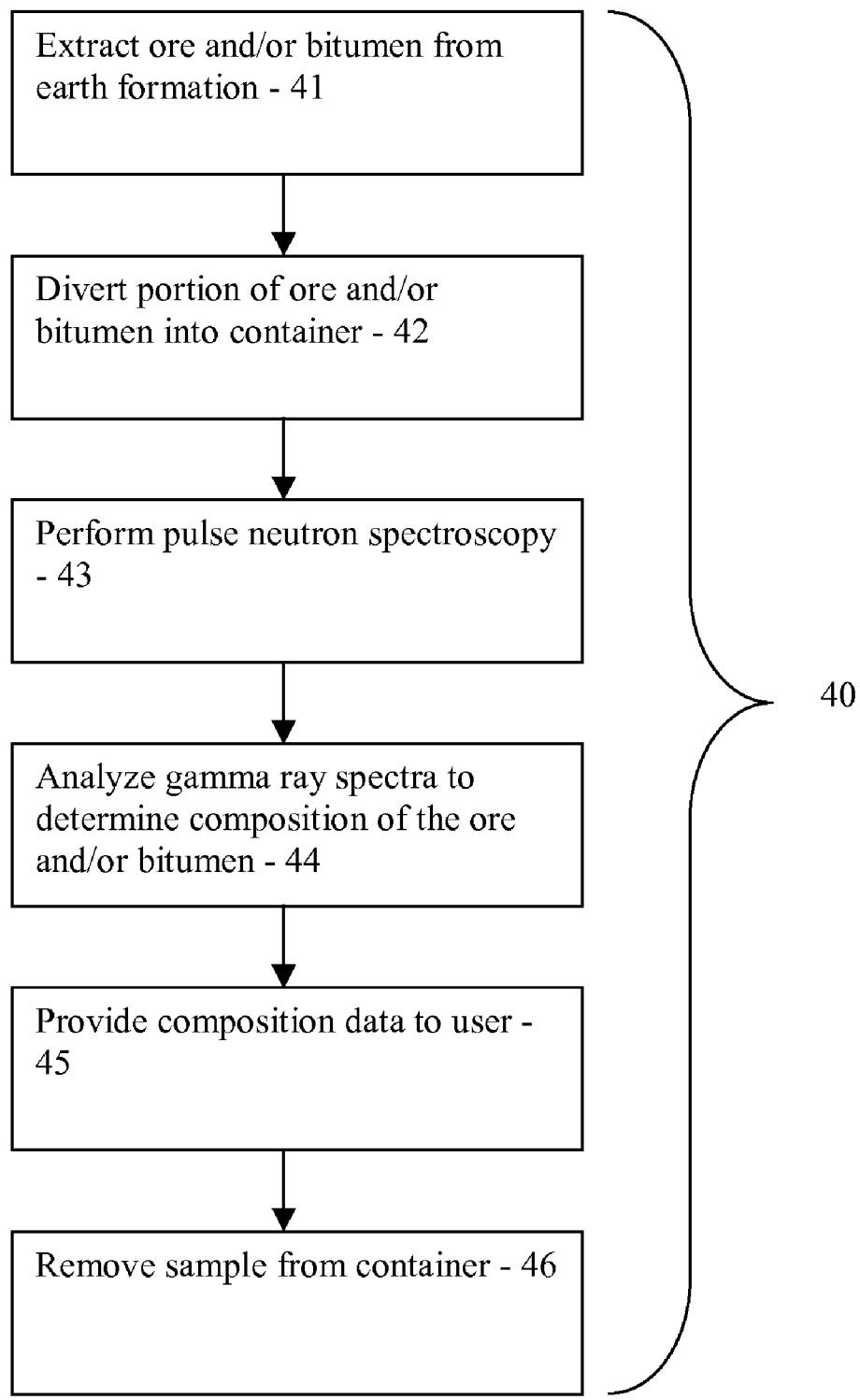
FIG. 3 is a flow chart providing an exemplary method of measuring a composition of an earth formation.

FIG. 3 illustrates a method 40 for measuring a composition of hydrocarbon and other material extracted from an earth formation. The method 40 includes one or more of stages 41-46 described herein. The method may be performed continuously or intermittently as desired. The method is described herein in conjunction with the tool 24, although the method may be performed in conjunction with any number and configuration of processors, sensors and tools. The method may be performed by one or more processors or other devices capable of receiving and processing measurement data, such as the remote processor 25 or the electronics unit 36. In one embodiment, the method includes the execution of all of stages 41-46 in the order described. However, certain stages 41-46 may be omitted, stages may be added, or the order of the stages changed.

In the first stage 41, a batch of ore and/or bitumen 14 is extracted from an earth formation. In one embodiment, the ore 14 is extracted by a surface mining procedure. In other embodiments, the ore 14 is extracted from any suitable procedure including well extraction such as SAGD, and underground mining operations. In one example, the ore 14 is extracted in batches and loaded onto vehicles for transport to a processing station or processing plant. In another example, extraction is performed by a shovel-and-truck system, utilizing extraction machines such as power shovels and transport vehicles such as dump trucks.

In the second stage 42, a portion or sample of the ore 14 is removed from the batch and diverted into the container 12 including the pulse neutron spectroscopy assembly 22.

In the third stage 43, pulsed neutron spectroscopy is performed on the ore 14. A stream of high-energy neutrons from the neutron source 30 bombards the ore 14 and causes the ore 14 to generate a gamma ray spectrum. The gamma ray spectrum is detected by the radiation detector 32.

In the fourth stage 44, the gamma ray spectrum or spectra are analyzed to determine selected constituents including elements such as Carbon, Silica, Sulfur, Chlorine, Magnesium and Aluminum. In one embodiment, the spectra are analyzed either by counting gamma rays in windows placed at the main peaks for the elements concerned. Peaks at selected energy levels indicate the presence of corresponding elements. In another embodiment, the spectra are analyzed by comparing a spectrum pattern with gamma ray spectrum patterns for known elements and/or concentrations. In yet another embodiment, both types of analysis are utilized in a joint analysis referred to as "alpha processing".

In the fifth stage 45, the resulting composition data is provided to a user and may be used to monitor and/or adjust parameters related to processing the ore 14 to extract oil. In one embodiment, the data is stored in the tool 24 and/or transmitted to a processor such as the processing unit 25, and can be retrieved therefrom and/or displayed for analysis. As used herein, a "user" may include an extraction process operator, a processing unit and/or any other entity selected to retrieve the data and/or control processing of the bitumen to produce oil.

In the sixth stage 46, the door 20 is opened and the ore 14 is unloaded from the container 12 due to gravity. The sample ore 14 may then be transported to the plant for processing.

The method 40 is performed continuously or intermittently during the extraction process. For example, each vehicle load is sampled to continuously monitor the composition of the ore 14 and the presence of selected constituent elements or combinations of elements.

In one embodiment, the method 40 is performed during an extraction operation and yields real time information regarding the composition of the ore 14. As used herein, generation of data in "real-time" is taken to mean generation of data at a rate that is useful or adequate for making decisions during or concurrent with processes such as extraction as may be opted for by a user or operator. As a non-limiting example, real-time measurements and calculations may provide users with information necessary to make desired adjustments during the extraction process.

Generally, some of the teachings herein are reduced to an algorithm that is stored on machine-readable media. The algorithm is implemented by a computer or processor such as the remote processor 25 or the electronics unit 36 and provides operators with desired output.

The systems and methods described herein provide various advantages over prior art techniques. The systems and methods allow for advance knowledge in real time or near real time of changes in the elemental make up of the bitumen and/or ore. Such knowledge can aid an operator in adjusting rates of oil production to increase efficiency and reduce the cost of production per unit of bitumen produced. Such knowledge can also prevent shutdowns or failures due to dramatic ore grade changes, which can result in plant shut downs that often result in several days production losses.

In support of the teachings herein, various analyses and/or analytical components may be used, including digital and/or analog systems. The system may have components such as a processor, storage media, memory, input, output, communications link, user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of monitoring a composition of hydrocarbon material extracted from an earth formation, the method comprising:
   extracting the hydrocarbon material from the earth formation;
   diverting a portion of the hydrocarbon material into a container, the container including a pulse neutron spectroscopy tool disposed therein;
   emitting a plurality of pulses of high-energy neutrons from the pulse neutron spectroscopy tool into the portion of the hydrocarbon material and inducing at least one gamma ray spectrum from the portion;
   detecting the at least one gamma ray spectrum at the pulse neutron spectroscopy tool; and
   calculating a composition of the hydrocarbon material based on the at least one gamma ray spectrum.

2. The method of claim 1, wherein calculating the composition includes calculating a concentration of at least one selected constituent.

3. The method of claim 2, wherein the at least one selected constituent is selected from at least one of Carbon, Silica, Sulfur and Chlorine, Magnesium and Aluminum.

4. The method of claim 1, wherein calculating the composition includes comparing the at least one gamma ray spectrum to known spectrum values corresponding to known constituents.

5. The method of claim 4, wherein comparing the at least one gamma ray spectrum includes at least one of counting gamma rays in windows placed at peaks corresponding to selected elements and comparing spectral patterns in the at least one gamma ray spectrum to known spectral patterns corresponding to known elements.

6. The method of claim 1, wherein the gamma ray spectrum is selected from at least one of an inelastic spectrum emitted due to inelastic neutron scattering and fast-neutron reactions and a capture spectrum due to neutron capture.

7. The method of claim 1, wherein the pulse neutron spectroscopy tool is disposed within a housing, the housing is disposed in an interior of the container and includes an opening at a bottom portion of the housing, the plurality of pulses are emitted through the opening and the gamma ray spectrum is detected through the opening.

8. The method of claim 7, further comprising accessing the pulse neutron spectroscopy tool through a section of the housing extending to an exterior of the container.

9. The method of claim 1, further comprising providing the composition to a user and adjusting a processing rate of the hydrocarbon material based on the composition.

10. The method of claim 1, wherein extracting the hydrocarbon material includes surface mining the earth formation.

11. A system for monitoring a composition of hydrocarbon material extracted from an earth formation, the system comprising:
    a container configured to receive a portion of the hydrocarbon material extracted from the earth formation;
    a protective housing disposed in the container;
    a pulsed neutron spectroscopy tool disposed in the housing and including at least one neutron generator configured to emit a plurality of pulses of high-energy neutrons into an interior of the container and at least one radiation detector configured to detect at least one gamma ray spectrum produced in response to the stream of high energy neutrons; and
    a processor configured to calculate a composition of the hydrocarbon material based on the at least one gamma ray spectrum.

12. The system of claim 11, wherein the pulsed neutron spectroscopy tool is disposed within a housing, and the housing is disposed in an interior of the container.

13. The system of claim 12, wherein the housing includes an opening at a bottom portion of the housing.

14. The system of claim 13, wherein neutron generator is configured to emit the plurality of pulses through the opening and the radiation detector is configured to detect the at least one gamma ray spectrum through the opening.

15. The system of claim 11, wherein the processor is configured to calculate a concentration of at least one selected constituent.

16. The system of claim 15, wherein the at least one selected constituent is selected from at least one of Carbon, Silica, Sulfur, Chlorine, Magnesium and Aluminum.

17. The system of claim 11, wherein the housing extends to an exterior of the container and is configured to allow direct access to the pulsed neutron spectroscopy tool through the housing.

18. The system of claim 11, wherein the processor is configured to calculate the composition by comparing the at least one gamma ray spectrum to known spectrum values corresponding to known constituents.

19. The system of claim 11, wherein the gamma ray spectrum is selected from at least one of an inelastic spectrum emitted due to inelastic neutron scattering and fast-neutron reactions and a capture spectrum due to neutron capture.

20. The system of claim 11, wherein the hydrocarbon material is extracted from the earth formation by a surface mining process.

* * * * *